US008344164B2

(12) United States Patent
Hwang et al.

(10) Patent No.: US 8,344,164 B2
(45) Date of Patent: Jan. 1, 2013

(54) POLYHETEROCYCLIC COMPOUND, ORGANIC ELECTRONIC DEVICE USING POLYHETEROCYCLIC COMPOUND, AND ELECTRONIC APPARATUS INCLUDING ORGANIC ELECTRONIC DEVICE

(75) Inventors: In-Ho Hwang, Daejeon (KR); Min-Jeong Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 651 days.

(21) Appl. No.: 12/308,670

(22) PCT Filed: Jun. 20, 2007

(86) PCT No.: PCT/KR2007/002975
§ 371 (c)(1),
(2), (4) Date: Dec. 19, 2008

(87) PCT Pub. No.: WO2007/148914
PCT Pub. Date: Dec. 27, 2007

(65) Prior Publication Data
US 2010/0240910 A1    Sep. 23, 2010

(30) Foreign Application Priority Data
Jun. 20, 2006  (KR) .................. 10-2006-0055434

(51) Int. Cl.
*C07D 409/14*  (2006.01)
(52) U.S. Cl. ....................................... 549/59
(58) Field of Classification Search ............... 549/59
See application file for complete search history.

(56) References Cited

U.S. PATENT DOCUMENTS

| | | | |
|---|---|---|---|
| 5,543,257 | A | 8/1996 | Suzuki et al. |
| 2003/0137240 | A1 | 7/2003 | Hartmann et al. |
| 2003/0235713 | A1 | 12/2003 | Suzuki et al. |
| 2006/0229431 | A1 | 10/2006 | Kanitz et al. |
| 2009/0159876 | A1 | 6/2009 | Ohba et al. |

FOREIGN PATENT DOCUMENTS

| | | |
|---|---|---|
| JP | 63-183451 | 7/1988 |
| JP | 07-199494 | 8/1995 |
| JP | 2003-77670 | 3/2003 |
| JP | 2003-520795 | 7/2003 |
| JP | 2003-282268 | 10/2003 |
| JP | 2005-063679 | 3/2005 |
| JP | 2005-082532 | 3/2005 |
| JP | 2007-116115 | 5/2007 |
| WO | WO 02-21611 | 3/2002 |
| WO | WO 2004/099291 | 11/2004 |

OTHER PUBLICATIONS

Sato et al., Preparation of poly(3,3'-dialkynyl-2,2'-bithiophene-5,5'-diyl) with high coplanarity and effective pi-conjugation system, 2006, Polymer, 47, 37-41.*
Almutairi et al., ortho-Tetraaryls as helical building blocks: a study of structure, theory, electrochemistry, and optical properties, 2004, Tetrahedron, 60, 7187-7190.*
Gallazzi et al., Polythiophenes with Unusual Electrical and Optical Properties Based on Donor Acceptor Alternance Strategy, 2001, Macromolecular Chemistry and Physics, 202, 2074-2085.*
"Characterization, Supermolecular Assembly and Nanostructures of Thiophene Dendrimers" Xia, et al; American Chemical Society 2004, 126, 8735-8743.
"New Air-Stable $_n$-Channel Organic Thin Film Transistors" Bao, et al.; Journal of American Chemical Society 1998, 120 (1), 207-208.
"Building Blocks for n-Type Organic Electronics: Regiochemically Modulated Inversion of Majority Carrier Sign in Perflouroarene-Modified Polythiophene Semiconductors" Facchetti, et al. ; Agnew Chem. Int. Ed. 2003, 42, 3900-3903.
"Organic Electronics" Shaw, et al. IBM J. Res & Dev. vol. 45 No. 1 Jan. 2001.
"Macromolecular Electronic Device: Field-Effect Transistor with a Polythiophene Thin Film" Tsumura, et al; Appl. Phys. Lett 49 (18), Nov. 3, 1986.
"Synthetic Chemistry for Ultrapure, Processable, and High-Mobility Organic Transistor Semiconductors" Katz, et al.; Acc Chem. Res., 2001, 34 (5) 359-369.
Rapta et al. "Thiophene-Thiophene verses Phenyl-Phenyl Coupling in 2-(Diphenylamino)-Thiophenes: An ESR-UV/Vis/NIR Spectroelectrochemmical Study", ChemPhysChem, 2006, 7(4), 863-870.
Zeika et al. "On the oxidative coupling of N,N-disubstituted 2-aminothiophenes-synthesis of N,N'-persubstituted 5,5'-diamino-2,2'-bithiophenes", Tetrahedron, 2004, 60(37), 8213-8219.
Wong et al. "Synthesis and properties of novel bis(triarylamines) based on a 3,3'-diphenyl-2,2'bithiophene core", Chemical Communication, 2001, (17), 1628-1629.
Naudin et al. "Poly(3-arylthiophenes): Syntheses of Monomers and Spectroscopic and Electrochemical Characterization of the Corresponding Polymers", Chemistry of Materials, 2001, 13(2), 634-642.
Lin et al. "Synthesis and characterization of alternating fluorine-based copolymers containing diaryl- and non-substituted bithiophene units", Polymer, 2005, 46(23), 9810-9820.
Almutairi et al. "Molecular springs and muscles: Progress toward augmented electromechanical actuation", Pure and Applied Chemistry, 2006, 78(4), 777-781.
Dohi et al. "Direct Synthesis of Bipyrroles using phenyliodine Bis(trifluoroacetate) with Bromotrimethylsilane", Organic Letters, 2006, 8(10), 2007-2010.
Sato et al. "Preparation of poly(3,3'-dialkyny1-2,2'-bithiophene-5,5'-diyl) with high coplanarity and effective π-conjugation system", Polymer, 2006, 47(1), 37-41.
Marsella et al. "Helical Sexithiophenes: An experimental and theoretical study implication the alternating 2,2':3,3' Regioisomer as a reliable helical motif", Journal of the American Chemical Society, 2003, 125(46).
Marsella et al. "Toward conjudated double helical ladder polymers: cyclooctatetrathiophene as a highly versatile double helical scaffold", Journal of the American Chemistry Society, 2000, 122(5), 974-975.
Dahlmann et al. "68 Palladium-catalyzed syntheses of polyethynyl-substitute 2,2'- bithiophenes", Helvetica Chimica Acta, 1996, 79(3), 755-766.

* cited by examiner

*Primary Examiner* — Kristin Bianchi
(74) *Attorney, Agent, or Firm* — McKenna Long & Aldridge LLP

(57) ABSTRACT

Disclosed is a novel polyheterocyclic compound, an organic electronic device using the polyheterocyclic compound, and an electronic apparatus including the organic electronic device. The polyheterocyclic compound has excellent solubility to solvent and high charge mobility. The organic electronic device produced by using the polyheterocyclic compound has excellent performance and is easily produced.

11 Claims, 3 Drawing Sheets

[Fig. 1]
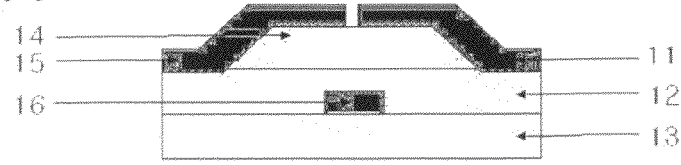
[Fig. 2]
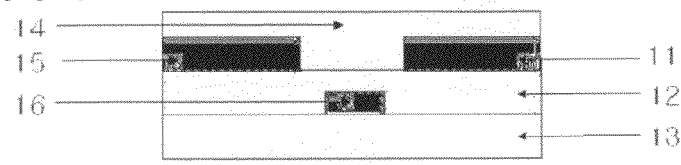
[Fig. 3]
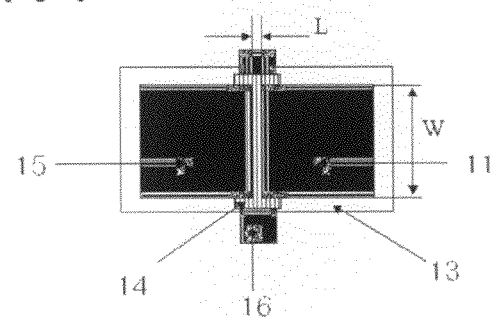
[Fig. 4]
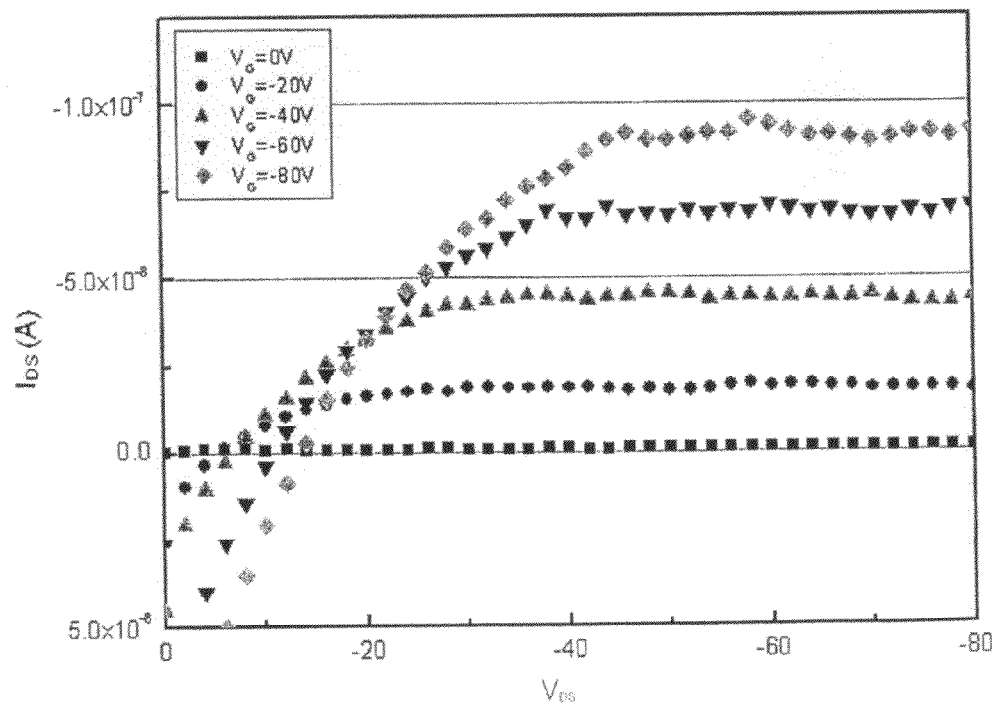

[Fig. 5]
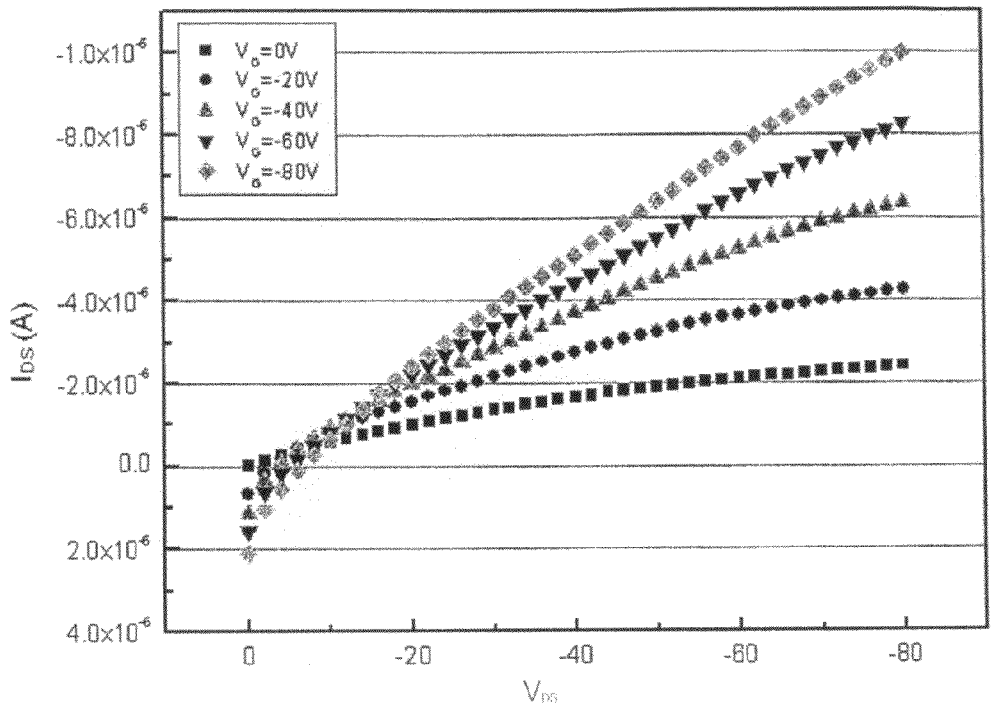
[Fig. 6]
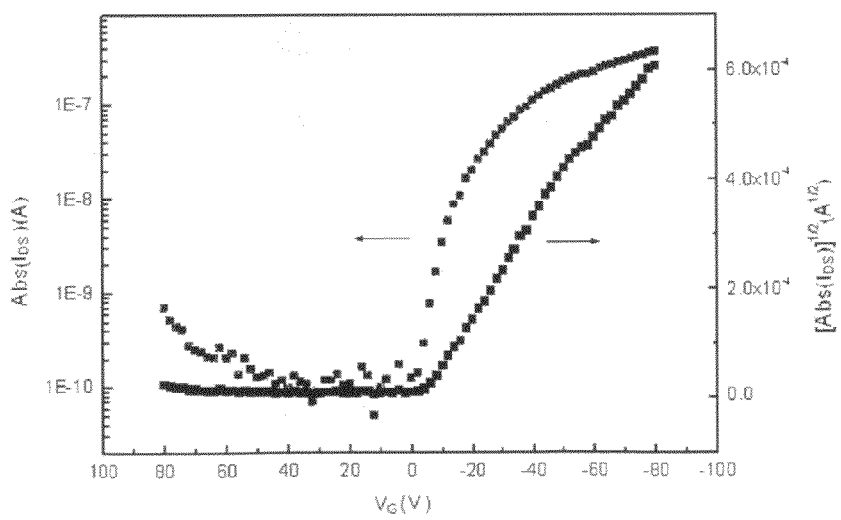

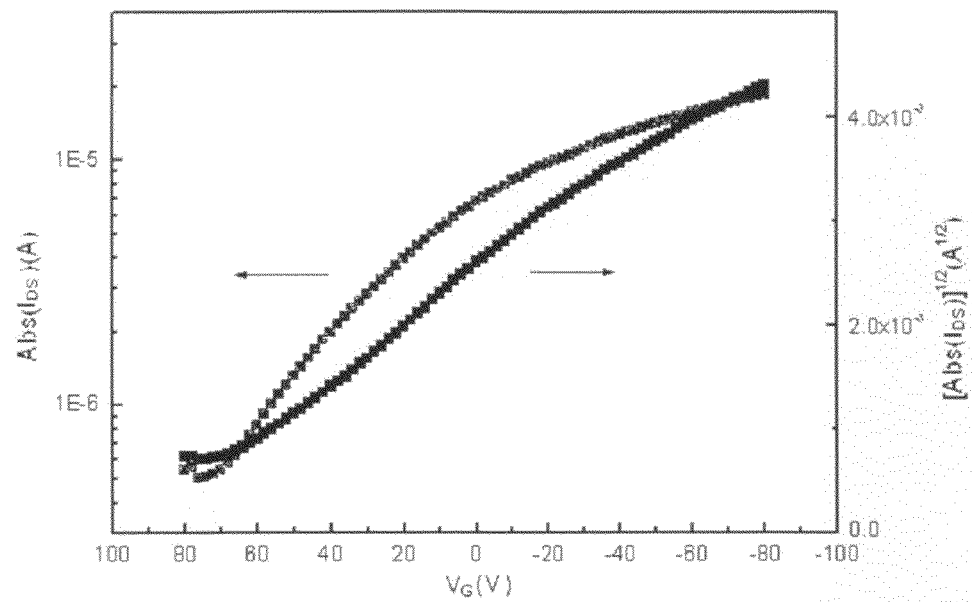
[Fig. 7]

POLYHETEROCYCLIC COMPOUND, ORGANIC ELECTRONIC DEVICE USING POLYHETEROCYCLIC COMPOUND, AND ELECTRONIC APPARATUS INCLUDING ORGANIC ELECTRONIC DEVICE

This application claims the benefit of PCT/KR2007/002975 filed on Jun. 20, 2007 and also Korean Patent Application No. 10-2006-0055434 filed on Jun. 20, 2006, the contents of which is hereby incorporated herein by reference in their entirety.

TECHNICAL FIELD

The present invention relates to a polyheterocyclic compound, an organic electronic device using the polyheterocyclic compound, and an electronic apparatus including the organic electronic device.

This application claims priority from Korean Patent Application No. 10-2006-0055434 filed on Jun. 20, 2006 in the KIPO, the disclosure of which is incorporated herein by reference in its entirety.

BACKGROUND ART

Many studies of organic semiconductor materials have been made since electric conductivity of an organic compound that was subjected to a predetermined doping process was known to be similar to that of copper in the year 1970s.

In recent years organic semiconductor compounds have been frequently applied to organic electronic devices such as organic thin film transistors (OTFT), organic light-emitting diodes (OLED), organic solar cells, an organic laser, an electromagnetic wave blocking film, capacitors, and memory devices in consideration of properties such as electric conductivity, lightness in weight, flexibility, and processability of the organic semiconductor compound.

A thin film transistor that is a kind of field-effect transistor (FET) is a basic structure used in the electronic engineering field, and extensively used as a switching display device such as a liquid crystal display. Most thin film transistor is produced by using polysilicon or amorphous silicon as a semiconductor substance. The production process using silicon includes a high temperature process, a high vacuum system process, and a patterning process using a complicated photolithography method.

However, in a process of producing an organic thin film transistor using an organic substance, a relatively low temperature process is performed and a thin film is formed by using a solution process, thus the thin film transistor is produced by using a simple process at low cost. Furthermore, since the organic thin film transistor using the organic substance is compatible with a plastic substrate, it is light in weight and capable of being used in flexible goods.

The organic thin film transistor includes a gate electrode, an insulating layer, source and drain electrodes, and an organic semiconductor layer. The amount of current between the source and the drain is controlled by voltage applied to the gate.

In respects to an operation mechanism of the organic thin film transistor, operation of a P-type organic semiconductor will be described. If positive voltage is applied to a gate, a negative charge is induced at an interface between an organic semiconductor and an insulating layer. In the case of the P-type organic semiconductor, since there is a significant difference between a LUMO level (lowest unoccupied molecular orbital level) and a Fermi level of an electrode, it is difficult to inject electrons to the organic semiconductor. Therefore, even if voltage is applied between the source and the drain, a current does almost not flow. In contrast, if negative voltage is applied to the gate, an accumulation layer into which a positive charge is induced is formed in the vicinity of the insulating layer due to electric field induction resulting from the applied voltage. Generally, since a HOMO level (highest occupied molecular orbital level) of the P-type organic semiconductor is similar to the Fermi level of the electrode, the positive charge may be easily injected from the electrode to the organic semiconductor. Since there are many conductible charge carriers between the source and the drain, the current may desirably flow. In this connection, a drain current is increased in proportion to a drain voltage. Furthermore, if the drain voltage is desirably increased, an electric potential is rapidly changed at the outskirts of the drain to form a depletion layer of electrons and saturate the drain current. Hence, even though the drain voltage is increased, the drain current is maintained.

The organic thin film transistor is evaluated by using performance indexes such as field-effect mobility ($\mu_{FET}$, □/V□sec), an on/off current ratio ($I_{on}/I_{off}$), a threshold voltage ($V_T$), a sub-threshold slope (SS, V/dec). The field-effect mobility means a speed (□/sec) of a charge in a unit electric field of 1 V/□ and relates to an operation speed of the transistor. This value is calculated by using a correlation graph of the drain current and the gate voltage. In a saturation state of the drain-source current, the field-effect mobility is calculated by using the following equation.

$$I_{DS} = \frac{WC_i}{2L}\mu_{FET}(V_G - V_T)^2 \qquad <\text{Equation}>$$

The above-mentioned equation is used to obtain the field-effect mobility in the saturation state of the drain-source current. $I_{DS}$ means the drain-source current in the saturation state, $\mu_{FET}$ means the field-effect mobility, $C_i$ means a capacitance per unit area of a gate insulator, $V_G$ means a gate voltage, and $V_T$ means a threshold voltage. In the equation, the performance of the organic thin film transistor may vary according to a channel length (L), a width (W), and a capacitance of the insulator of the organic thin film transistor shown in FIG. 3.

The on/off current ratio is defined by a ratio of current in a flow state and current in a cutoff state and an index of switching performance of the transistor. The threshold voltage is determined by a difference in work function of the gate and the organic semiconductor, an internal charge of a gate insulator, an interfacial charge, and the like. The sub-threshold slope is the magnitude of gate voltage required to increase the current 10 times at the threshold voltage and means an ability of controlling the interface of the organic semiconductor of the gate.

Many studies of electrode material, insulating layer material, organic semiconductor material have been made in order to improve the above-mentioned performance indexes. In connection with this, it is the most important and difficult to improve charge mobility of the organic semiconductor compound. The organic semiconductor compound has high crystallinity and the charge mobility thereof is increased as Π-orbit superposition is increased.

Many studies of substances and production processes have been made since the organic thin film transistor was reported by Tsumura et al. for the first time (A. Tsumura, K. Koezuka and T. Ando, Appl. Phys. Lett., 1986, 49, 1210). Organic substances such as low molecular weight substances, polymers, and oligomers have been studied to be used as semiconductor substances in the thin film transistor. As shown in the results of the studies, the performance of the organic thin film transistor is improved from $10^{-5}\square$/Vs to $1\square$/Vs in views of charge carrier mobility of the thin film transistor (J. M. Shaw, P. F. Seidler, IBM J. Res. & Dev., 2001, Vol. 45, 3). The performance of the current organic thin film transistor is similar to that of an amorphous silicon transistor, and the organic thin film transistor is used in display apparatuses such as E-papers, smart cards, sensors, electronic tags (radio frequency identification, RFID), liquid crystal displays, and organic light emitting diodes.

There are two types of molecules that are capable of being used to constitute a semi-conductor layer and they are p-type and n-type organic semiconductor substances. In the p-type semiconductor substance, a hole is a charge carrier and, in the n-type semi-conductor substance, an electron is the charge carrier. Examples of the p-type organic semiconductor substance include pentacene, antradithiophene, benzodithiophene, thiophene oligomer, polythiophene, mixed-subunit thiophene oligomer, and oxy-functionalized thiophene oligomer (H. E. Katz et al., Acc. Chem. Res. 2001, 34, 359). Examples of the n-type organic semiconductor substance include fluorinated metallophthalocyanine (Z. Bao, J. Am. Chem. Soc. 1998, 120, 207) and perfluoroarene-modified polythiophene (A. Facchetti, Angew. Chem. Int. Ed. 2003, 42, 3900).

Currently, pentacene, oligothiophene derivatives, poly[3-hexyl thiophene], and the like are used as a material that has the desirable performance and is most extensively used. However, pentacene and the oligothiophene derivative has the desirable performance only in the case of when a thin film is formed by using a vacuum deposition process, but is problematic in that it is not easy to perform a solution process. The thin film may be formed by means of the soluble oligothiophene derivative and polythiophene derivative using the solution process such as screen-printing, ink-jet printing, micro-contact printing, spin coating, and dip coating. However, the charge mobility is still worse than that of the thin film transistor that is produced by using vacuum deposition of the low molecular system and the on/off current ratio ($I_{on}/I_{off}$) is not enough to commercialize the organic thin film transistor.

Accordingly, in order to commercialize the organic thin film transistor, there remains a need to develop a low-priced organic semiconductor substance that is capable of being used during a solution process and has high charge mobility and on/off current ratio.

DISCLOSURE OF INVENTION

Technical Problem

Therefore, the present invention has been made keeping in mind the above problems occurring in the related art, and it is an object of the present invention to provide a novel polyheterocyclic compound that is easily synthesized, has acceptable process ability and high charge mobility and on/off current ratio, and is capable of being used as a semiconductor or charge transporting substance, an organic electronic device using the polyheterocyclic compound, and an electronic apparatus including the organic electronic device.

Technical Solution

The present invention provides a polyheterocyclic compound represented by Formula 1:

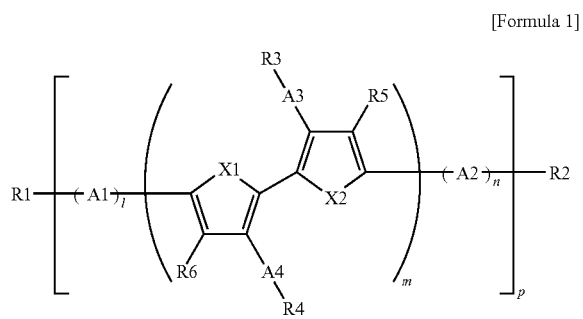

[Formula 1]

wherein
m is an integer in the range of 1 to 5, l and n are each independently an integer in the range of 0 to 5, p is an integer in the range of 1 to 10,000, X1 and X2 are each independently any one selected from S, O, NH, and NR, in which R of NR is any one selected from a substituted or unsubstituted $C_1$-$C_{60}$ alkyl group and a substituted or unsubstituted $C_6$-$C_{20}$ aryl group, A1 to A4 are each independently any one selected from a substituted or unsubstituted alkenyl group, a substituted or unsubstituted alkynyl group, a substituted or unsubstituted arylamine group, a substituted or unsubstituted aromatic or nonaromatic heterocyclic group, and a substituted or unsubstituted $C_6$-$C_{20}$ aryl group, and R1 to R6 are each independently any one selected from a hydrogen atom, halogen, a substituted or unsubstituted straight- or branch-chained $C_1$-$C_{12}$ alkyl group, a substituted or unsubstituted straight- or branch-chained $C_1$-$C_{12}$ alkoxy group, a substituted or unsubstituted straight- or branch-chained $C_1$-$C_{12}$ thioalkyl group, a substituted or unsubstituted arylamine group, a substituted or unsubstituted aromatic or nonaromatic heterocyclic group, and a substituted or unsubstituted $C_6$-$C_{20}$ aryl group.

Furthermore, the present invention provides an organic electronic device using the polyheterocyclic compound.

Furthermore, the present invention provides an electronic apparatus that includes an organic electronic device using the polyheterocyclic compound.

Advantageous Effects

A polyheterocyclic compound according to the present invention is a novel compound that has excellent solubility to a solvent and high charge mobility, and an organic electronic device that has the excellent performance and is capable of being easily produced is produced by using the polyheterocyclic compound. In particular, the polyheterocyclic compound is used to produce an organic thin film transistor having high field-effect mobility and on/off current ratio.

BRIEF DESCRIPTION OF THE DRAWINGS

FIG. 1 is a sectional view of a top-contact structure of an organic thin film transistor;

FIG. 2 is a sectional view of a bottom-contact structure of the organic thin film transistor;

FIG. 3 is a top view of the top-contact structure of the organic thin film transistor;

FIG. 4 is a graph showing a change in drain-source current ($I_{DS}$) to drain-source voltage ($V_{DS}$) in an organic thin film transistor of Example 1 of the present invention;

FIG. 5 is a graph showing a change in drain-source current ($I_{DS}$) to drain-source voltage ($V_{DS}$) in an organic thin film transistor of Comparative Example 1;

FIG. 6 is a graph showing a change in drain-source current ($I_{DS}$) to gate voltage ($V_G$) in the organic thin film transistor of Example 1 of the present invention; and FIG. 7 is a graph showing a change in drain-source current ($I_{DS}$) to gate voltage ($V_G$) in the organic thin film transistor of Comparative Example 1.

BEST MODE FOR CARRYING OUT THE INVENTION

A detailed description of the present invention will be given hereinafter.

The present invention provides a polyheterocyclic compound represented by Formula 1.

Substituent groups of Formula 1 will be described in detail.

Examples of alkyl that is a straight- or branch-chained include, but are not limited to, methyl, ethyl, propyl, butyl, pentyl, hexyl, heptyl, octyl, nonyl, decyl, undecyl, and dodecyl.

Examples of aryl include, but are not limited to, phenyl, biphenyl, terphenyl, benzyl, naphthyl, anthracenyl, tetracenyl, pentacenyl, perylenyl, pyrenyl, phenanthrenyl, and coronenyl.

Examples of alkenyl include, but are not limited to, ethenylene (vinylene).

Examples of alkynyl include, but are not limited to, ethynylene and diacetylene.

Examples of the aromatic or nonaromatic heterocyclic compound include, but are not limited to, thiophenyl, bithiophenyl, terthiophenyl, thienothiophenyl, thiazolothiazoline, furanyl, pyryl, imidazoline, oxazoline, oxadiazoline, thiazoline, pyridazinyl, pyrazinyl, and pyridyl.

Examples of alkoxy that is a straight- or branch-chained include, but are not limited to, methoxy, ethoxy, propoxy, butoxy, pentyloxy, hexyloxy, heptyloxy, octyloxy, nonyloxy, decyloxy, undecyloxy, and dodecyloxy.

Examples of thioalkyl that is a straight- or branch-chained include, but are not limited to, methylthio, ethylthio, propylthio, butylthio, pentylthio, hexylthio, heptylthio, octylthio, nonylthio, decylthio, undecylthio, and dodecylthio.

Examples of arylamine include, but are not limited to, diphenylamine, phenyl-naphtylamine, ditolylamine, phenyl-tolylamine, carbazol, and triphenylamine.

In the present invention, in the case of when an alkyl group, an aryl group, an alkenyl group, an alkynyl group, an aromatic or nonaromatic heterocyclic group, an arylamine group, an alkoxy group, or a thioalkyl group is substituted by the other substituent groups, each of the substituent groups may be one or more selected from an alkyl group, an aryl group, an alkoxy group, an alkenyl group, an alkynyl group, an arylamine group, a heterocyclic group, a silane group, a boron group, an amino group, a nitrile group, a nitro group, a halogen group, an amide group, an ester group, a sulfonyl group, a sulfoxide group, a sulfonamide group, and a sulfonate group, and they may form an aromatic, aliphatic, or heterocyclic ring in conjunction with the adjacent groups.

In Formula 1, it is preferable that at least one of X1 and X2 be S.

In Formula 1, it is preferable that A1 to A4 be independently a substituted or unsubstituted conjugated group.

Particularly preferably, A1 to A4 are thienyl (thiophenyl), bithiophenyl, terthiophenyl, thienyl (thiophenyl) substituted by $C_1$-$C_6$ alkyl, alkynyl, thienyl-substituted alkynyl, bithiophenyl-substituted alkynyl, thienothiophenyl, or thiazolothiazoline.

In addition, R1 to R4 are thienyl (thiophenyl), bithiophenyl, bithiophenyl substituted by $C_1$-$C_6$ alkyl, or a substituted or unsubstituted slime group-substituted $C_2$-$C_6$ alkynyl.

The polyheterocyclic compound represented by Formula 1 may be a compound represented by Formula 2 or 3, but are not limited thereto.

[Formula 2]

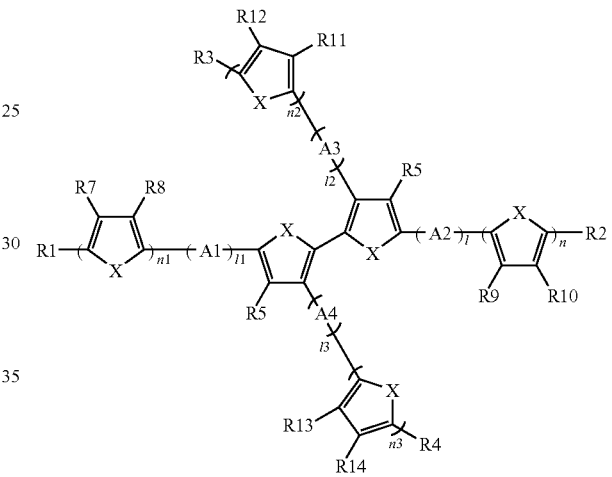

wherein l, l1, l2, l3, n, n1, n2, and n3 are each independently an integer in the range of 0 to 5, X is any one selected from S, O, NH, and NR, a plurality of Xs may be the same as or different from each other, in which R of NR is any one selected from a substituted or unsubstituted $C_1$-$C_{60}$ alkyl group, and a substituted or unsubstituted $C_6$-$C_{20}$ aryl group, A1 to A4 are each independently any one selected from a substituted or unsubstituted alkenyl group, a substituted or unsubstituted alkynyl group, a substituted or unsubstituted arylamine group, a substituted or unsubstituted aromatic or nonaromatic heterocyclic group, and a substituted or unsubstituted $C_6$-$C_{20}$ aryl group, and R1 to R14 are each independently any one selected from a hydrogen atom, halogen, a substituted or unsubstituted straight- or branch-chained $C_1$-$C_{12}$ alkyl group, a substituted or unsubstituted straight- or branch-chained $C_1$-$C_{12}$ alkoxy group, a substituted or unsubstituted straight- or branch-chained $C_1$-$C_{12}$ thioalkyl group, a substituted or unsubstituted arylamine group, a substituted or unsubstituted aromatic or nonaromatic heterocyclic group, and a substituted or unsubstituted $C_6$-$C_{20}$ aryl group.

[Formula 3]

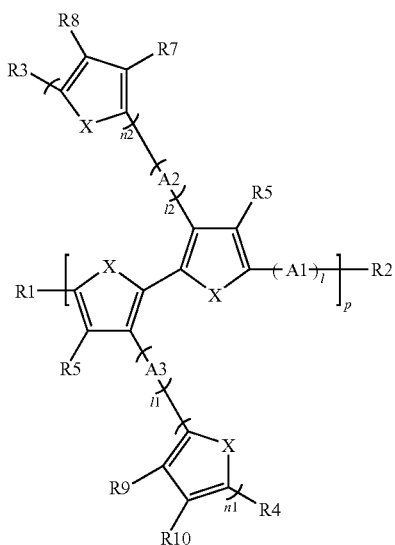

wherein l, l1, l2, n1, and n2 are each independently an integer in the range of 0 to 5 and p is an integer in the range of 1 to 10,000, X is any one selected from S, O, NH, and NR, a plurality of Xs may be the same as or different from each other, in which R of NR is any one selected from a substituted or unsubstituted $C_1$-$C_{60}$ alkyl group and a substituted or unsubstituted $C_6$-$C_{20}$ aryl group, A1 to A3 are each independently any one selected from a substituted or unsubstituted alkenyl group, a substituted or unsubstituted alkynyl group, a substituted or unsubstituted arylamine group, a substituted or unsubstituted aromatic or nonaromatic heterocyclic group, and a substituted or unsubstituted $C_6$-$C_{20}$ aryl group, and R1 to R10 are each independently any one selected from a hydrogen atom, halogen, a substituted or unsubstituted straight- or branch-chained $C_1$-$C_{12}$ alkyl group, a substituted or unsubstituted straight- or branch-chained $C_1$-$C_{12}$ alkoxy group, a substituted or unsubstituted straight- or branch-chained $C_1$-$C_{12}$ thioalkyl group, a substituted or unsubstituted arylamine group, a substituted or unsubstituted aromatic or nonaromatic heterocyclic group, and a substituted or unsubstituted $C_6$-$C_{20}$ aryl group.

Specific examples of the polyheterocyclic compound include, but are not limited to, the compounds represented by Formulae 1-1 to 1-25.

[Formula 1-1]

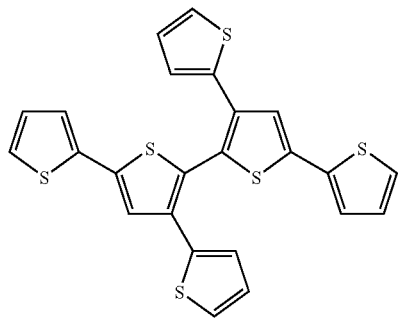

[Formula 1-2]

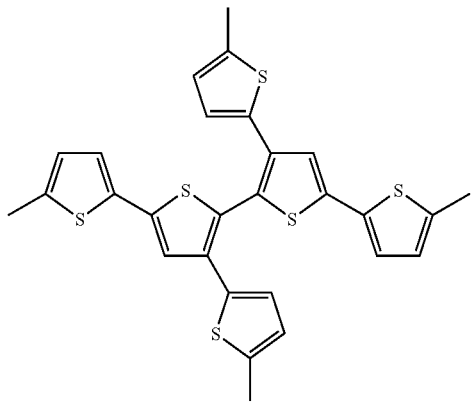

[Formula 1-3]

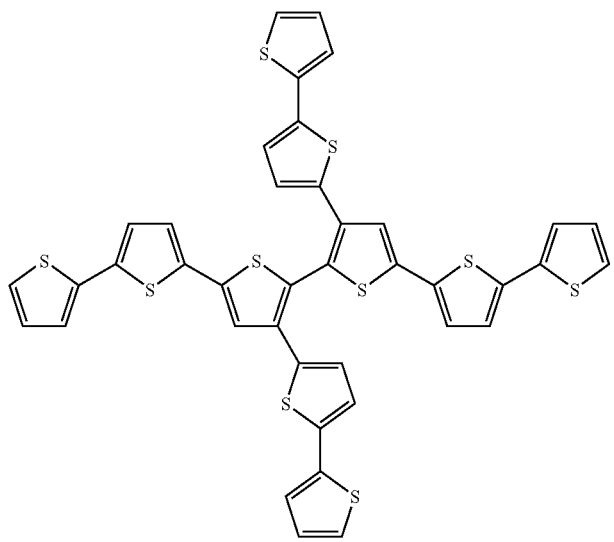

[Formula 1-4]
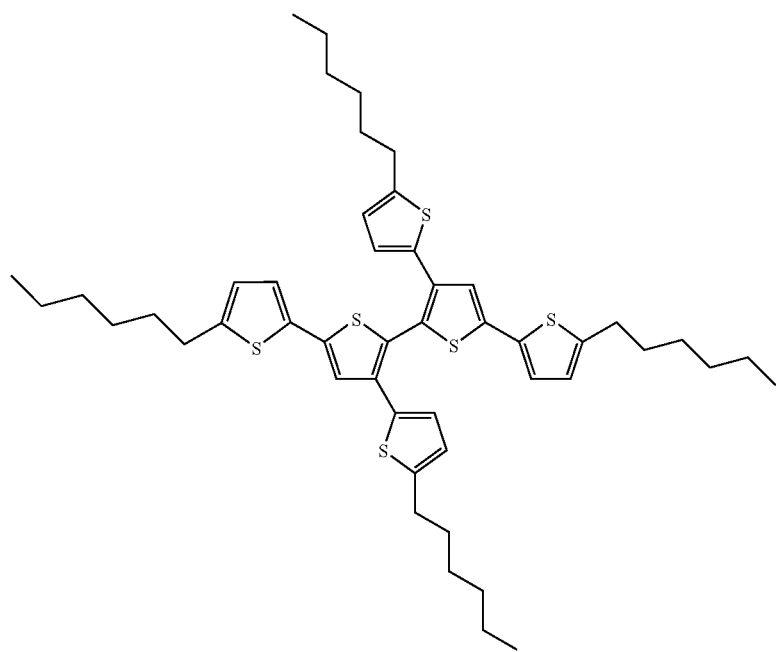
[Formula 1-5]
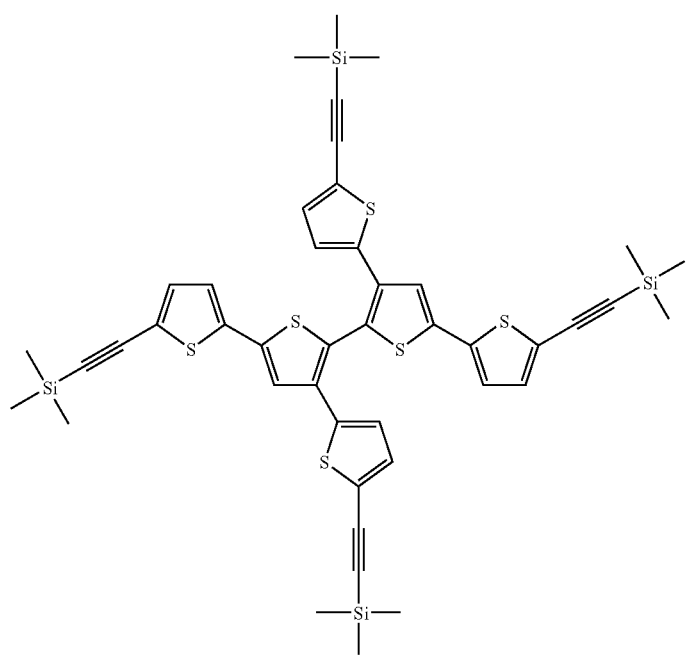

[Formula 1-6]
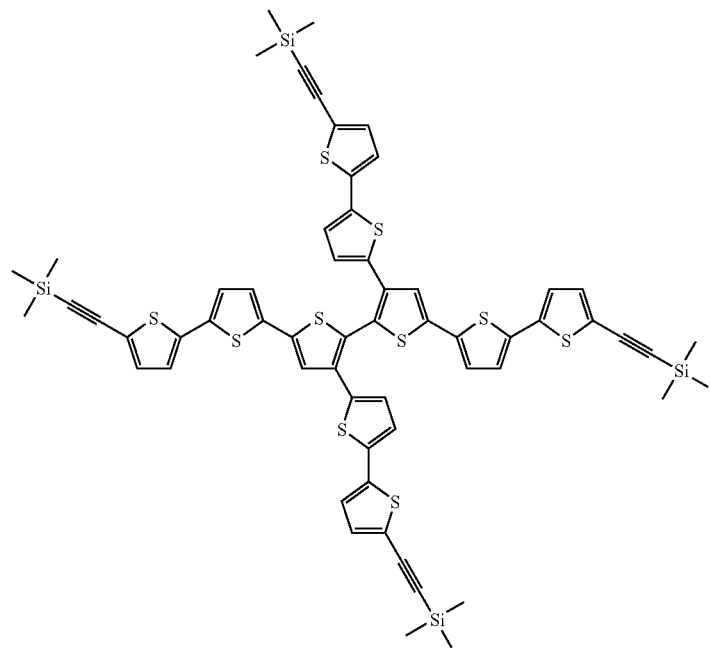
[Formula 1-7]
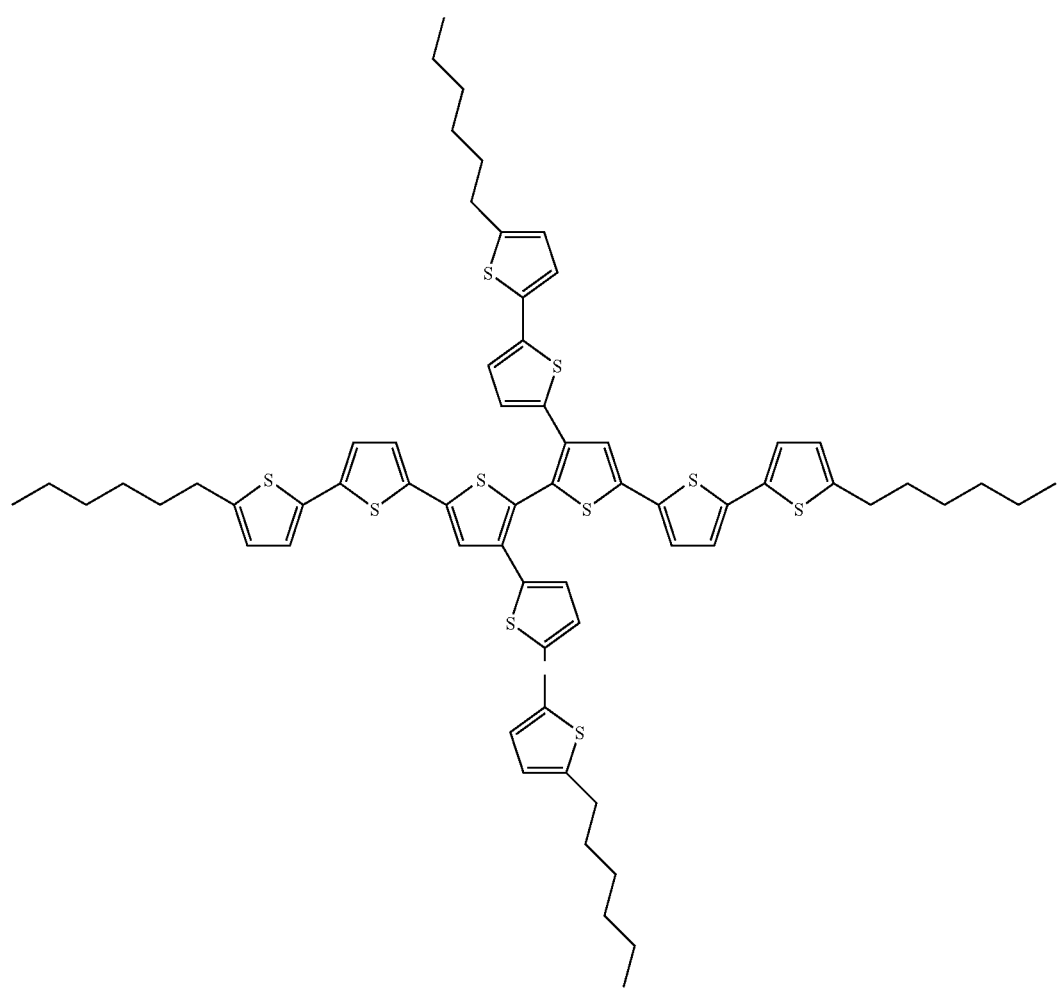

[Formula 1-8]
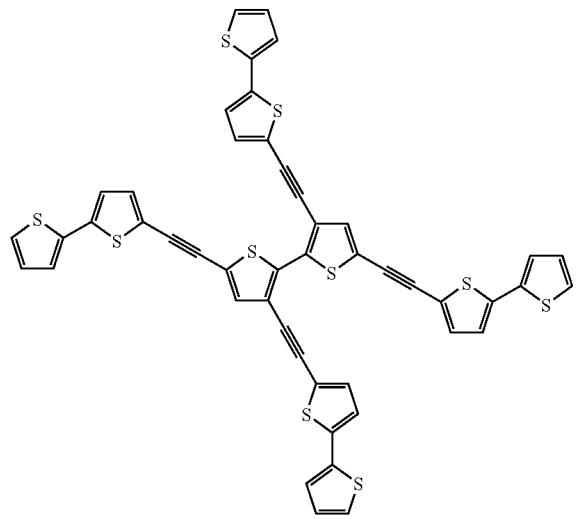
[Formula 1-9]
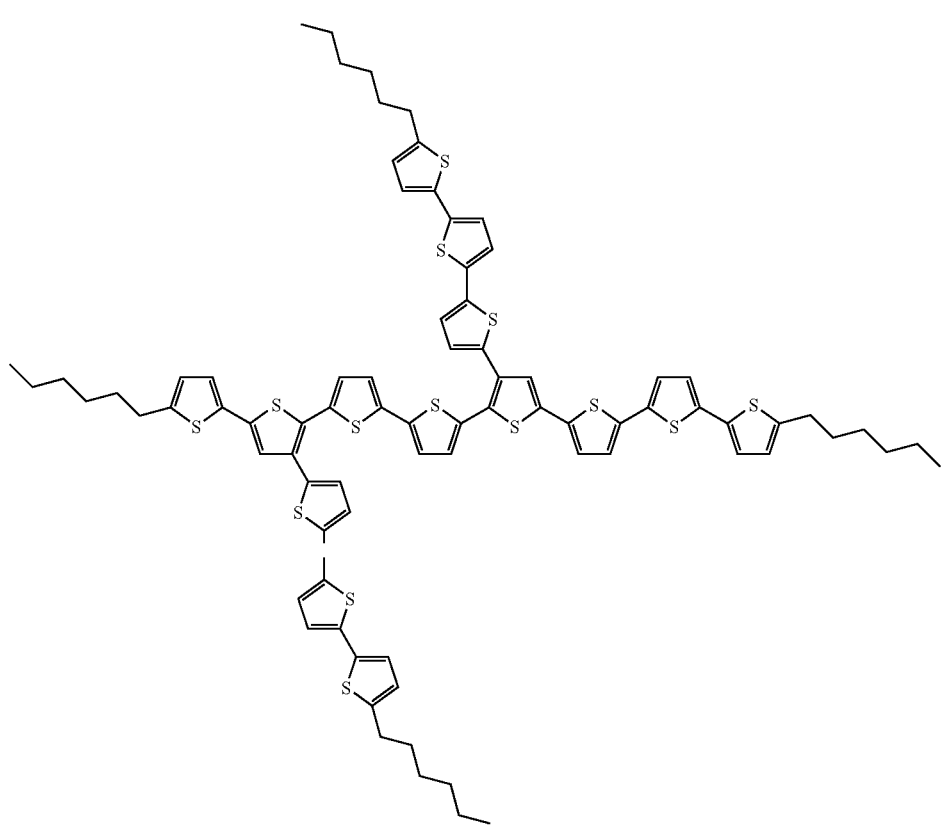

-continued
[Formula 1-10]
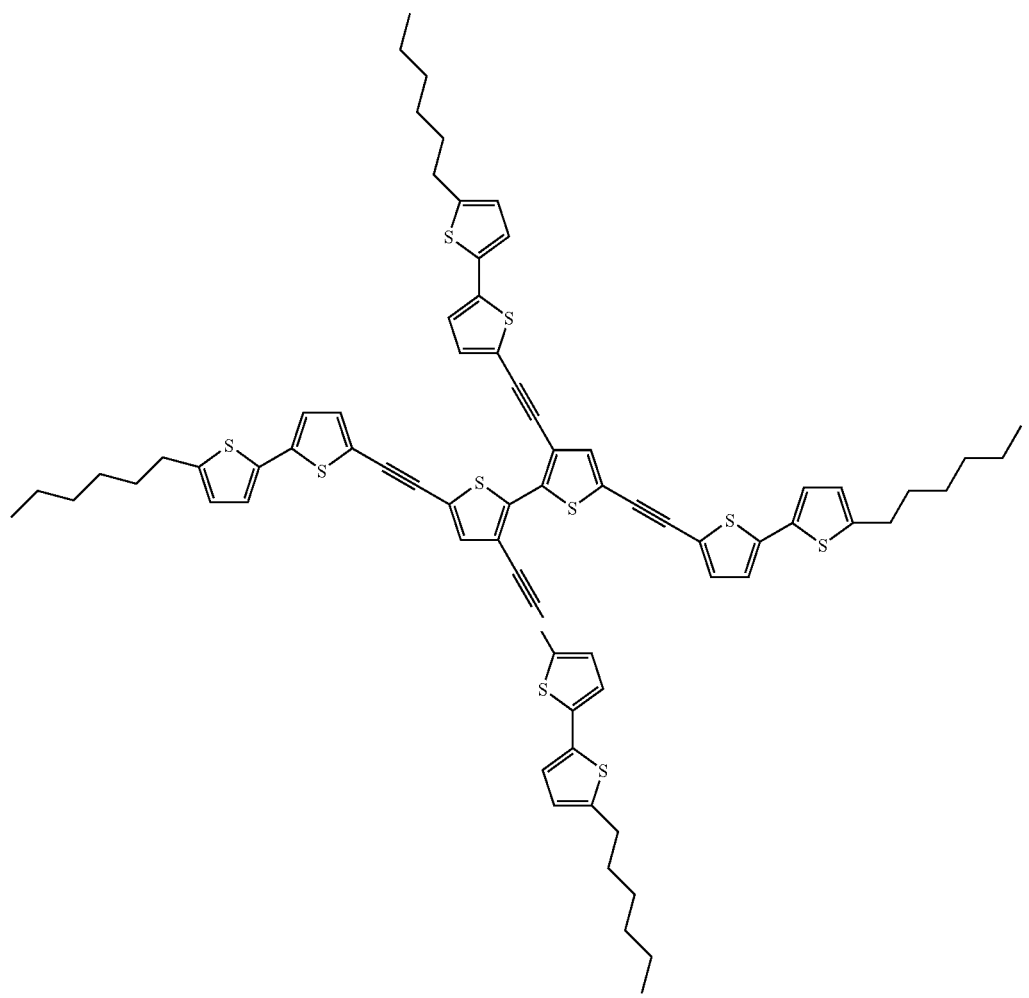
[Formula 1-11]
[Formula 1-12]
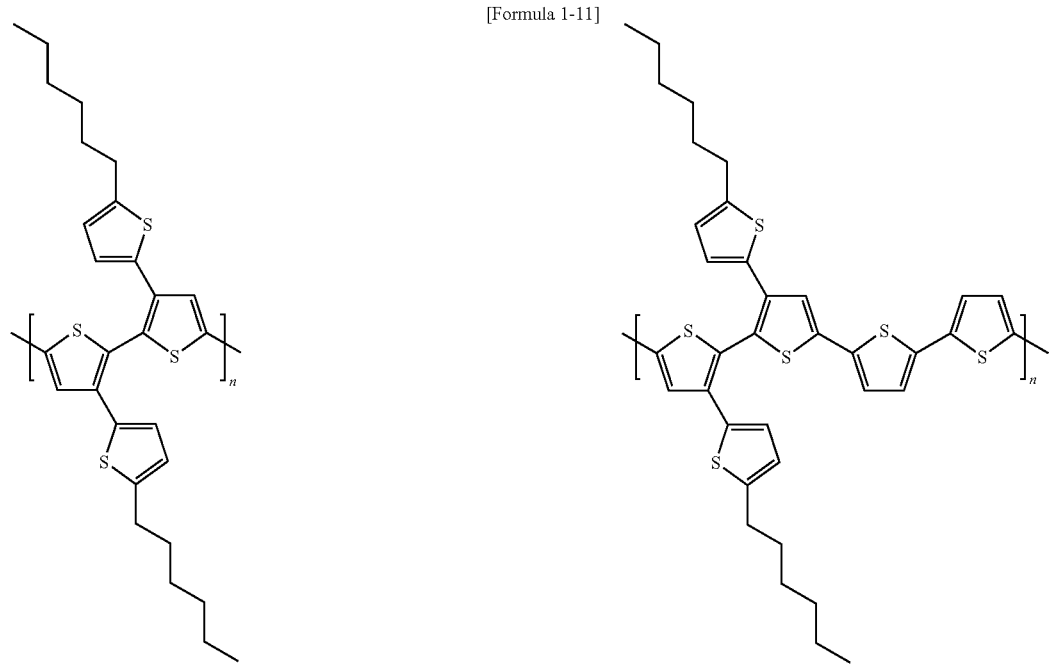

[Formula 1-13]
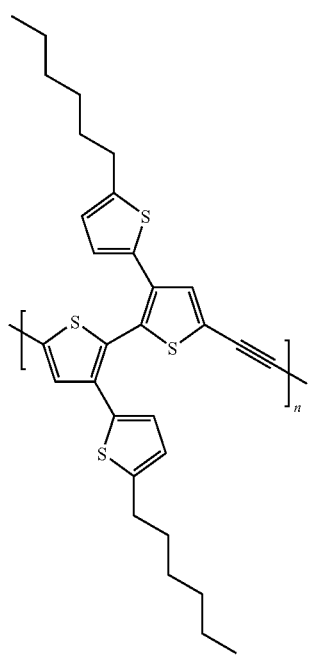
[Formula 1-14]
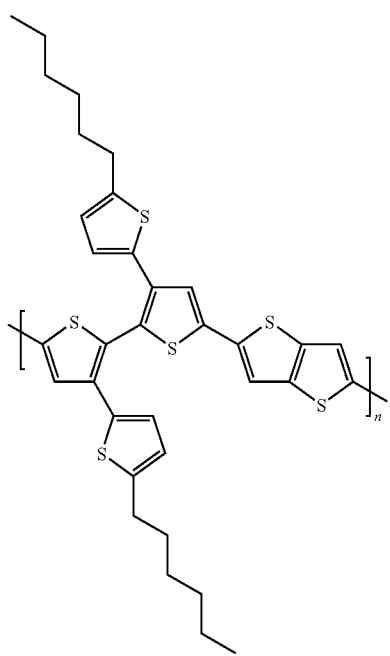
[Formula 1-15]
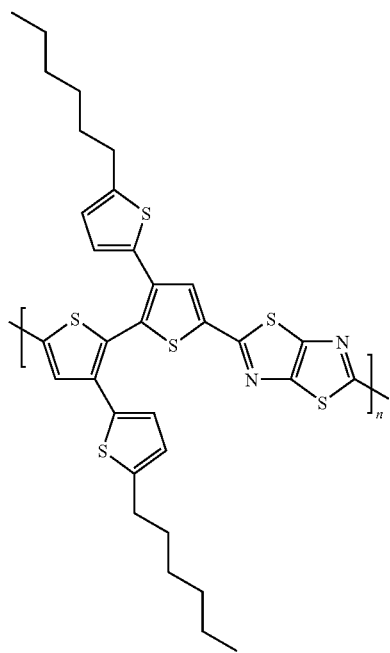
[Formula 1-16]
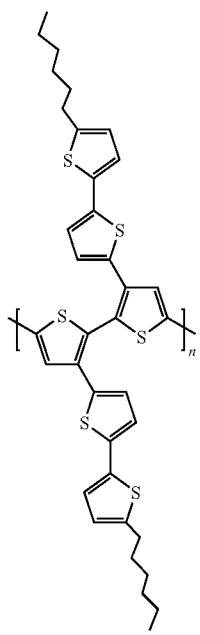

[Formula 1-17]
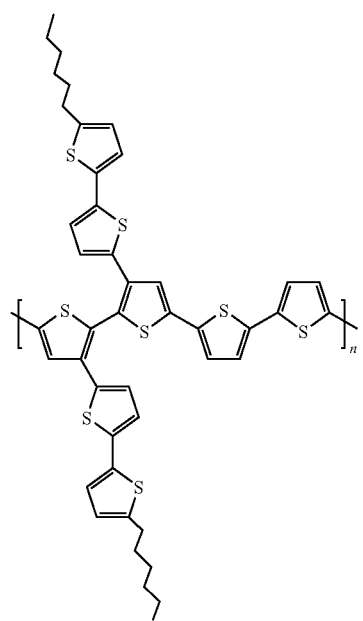
[Formula 1-18]
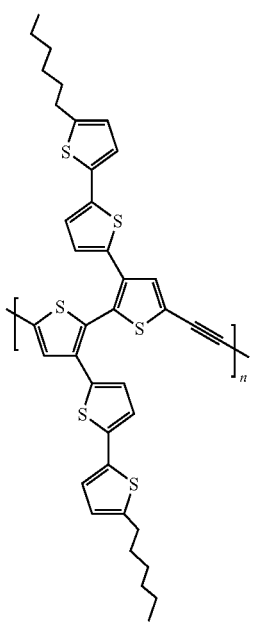
[Formula 1-19]
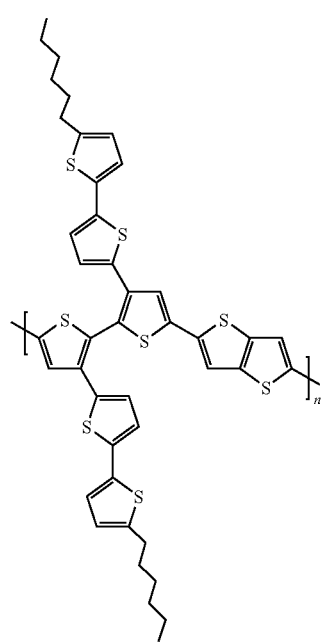
[Formula 1-20]
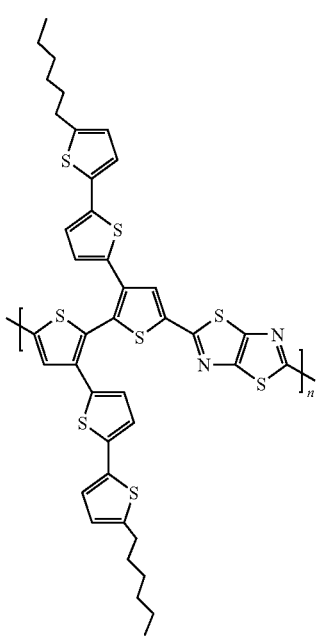

-continued
[Formula 1-21]
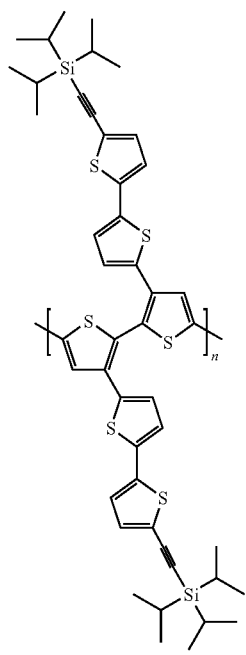
[Formula 1-22]
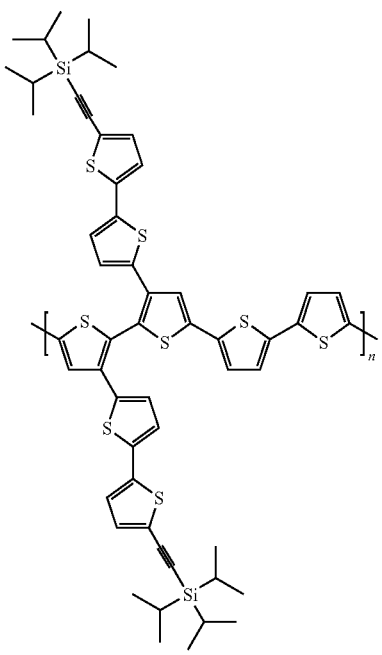
[Formula 1-23]
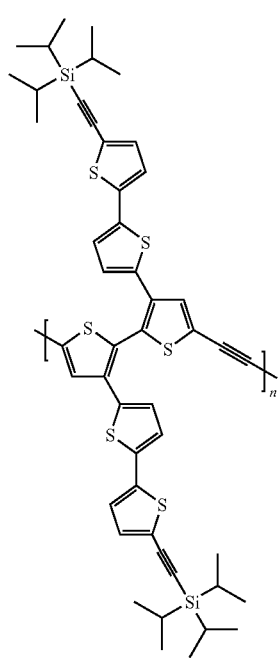
[Formula 1-24]
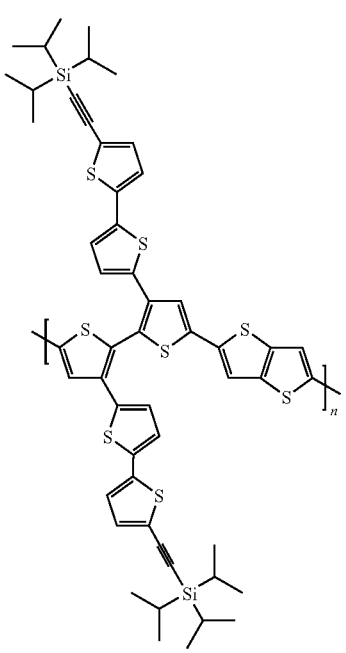

[Formula 1-25]

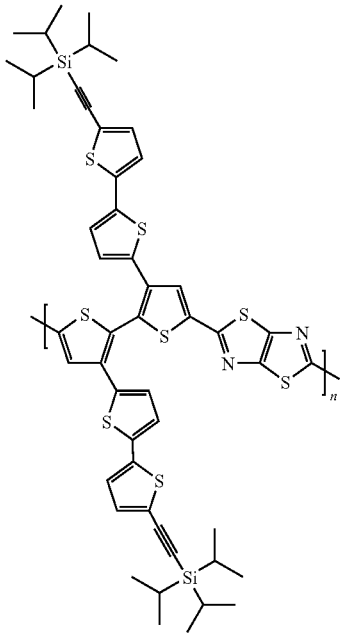

Since the polyheterocyclic compound according to the present invention contains the heterocyclic group, particularly the thiophene group, characteristics of the organic semiconductor may be obtained.

The polyheterocyclic compound represented by Formula 1 of the present invention may be produced by using the following method.

After a heterocyclic compound that is substituted by four halogen atoms (bromine, iodine, or the like) is produced, the compound is subjected to a carbon-carbon bonding reaction such as a Suzuki reaction and a Stille reaction in conjunction with a substituent group which is to be added to produce the above-mentioned poly-heterocyclic compound. In the case of when the substituent group to be added is a boronic acid or boronic ester compound, the polyheterocyclic compound may be produced by using a Suzuki reaction and, in the case of when the substituent group to be added is a tributyltin compound, the polyheterocyclic compound may be produced by using a Stille reaction. However, the production of the polyheterocyclic compound is not limited thereto. In addition, after a heterocyclic compound that is substituted by two halogen atoms is produced by removing two halogen atoms from the heterocyclic compound that is substituted by four halogen atoms, the compound is subjected to a carbon-carbon bonding reaction such as a Suzuki reaction and a Stille reaction in conjunction with a substituent group which is to be added so as to produce monomers that are capable of being polymerized. The monomers may be polymerized by means of an oxidation polymerization process using iron trichloride ($FeCl_3$) or a polymerization process using various types of metal catalysts containing nickel, magnesium, zinc, or the like to form a polymer contained in the compound, but are not limited thereto.

Furthermore, the present invention provides an organic electronic device using the polyheterocyclic compound. Examples of the organic electronic device include an organic thin film transistor, an organic light emitting diode, an organic solar cell, an organic laser, an electromagnetic wave blocking film, a capacitor, and a memory device.

The organic thin film transistor that belongs to the organic electronic device of the present invention will be described in detail.

The organic thin film transistor is classified into a top-contact structure and a bottom-contact structure according to the type of contact between the organic semiconductor layer and the source and drain electrodes. FIG. 1 is a sectional view of a top-contact structure in which an upper side of an organic semiconductor layer 14 is in contact with a source electrode 15 and a drain electrode 11. FIG. 2 is a sectional view of a bottom-contact structure in which a lower side of the organic semiconductor layer 14 is in contact with the source electrode 15 and the drain electrode 11. The organic thin film transistor of the present invention includes a substrate, a gate electrode, an insulating layer, a semiconductor layer, and source and drain electrodes.

The substrate 13 may be made of glass, a semiconductor wafer, metal oxide, a ceramic substance, plastic, or the like that is capable of satisfying thermodynamic and mechanical requirements for the organic thin film transistor.

The insulating layer 12 is made of an insulating substance, and examples of the insulating substance include but are not limited to silicon oxide and silicon nitride; and a plastic insulator such as polyimide, poly(2-vinylpyridine), poly(4-vinylphenol), and polymethyl methacrylate.

The compound that is represented by Formula 1 is used in the organic semiconductor layer 14, and specific examples of the compound include but are not limited to the compounds represented by Formulae 1-1 to 1-25. The semiconductor layer may be formed by using a solution process such as screen-printing, ink-jet printing, micro-contact printing, spin coating, dip coating, and SAM (self-assembled monolayer).

The gate electrode 16, the source electrode 15, and the drain electrode 11 are made of a conductive substance, and examples of the conductive substance include but are not limited to carbon, aluminum, vanadium, chromium, copper, zinc, silver, gold, magnesium, calcium, sodium, potassium, titanium, indium, yttrium, lithium, gadolinium, tin, lead, neodymium, platinum, similar metals, and alloys of the metals; p- or n-doped silicon; zinc oxide, indium oxide, indium tin oxide (ITO), indium zinc oxide, similar tin oxide, and tin oxide indium-based complex compounds; a mixture of oxide and metal such as ZnO:Al and $SnO_2$:Sb; and a polymer such as poly(3-methylthiophene), poly[3,4-(ethylene-1,2-dioxy) thiophene], polypyrrole, and polyaniline.

In addition, the substance for the source electrode and the drain electrode has a pre-determined work function to reduce an injection barrier of a charge carrier and form an ohmic contact to the organic semiconductor layer. In the case of when a p-type substance is used in the semiconductor layer, the work function of the substance of the source electrode and the drain electrode corresponds to or is very similar to a HOMO (highest occupied molecular orbital) energy level of the p-type organic substance. Therefore, it is preferable that metal having a very large work function such as palladium, platinum, and gold be used to produce the source electrode and the drain electrode. Meanwhile, in the case of when an n-type substance is used in the semi-conductor layer, the work function of the substance of the source electrode and the drain electrode corresponds to or is very similar to a LUMO (lowest unoccupied molecular orbital) energy level of the n-type organic substance. Therefore, it is preferable that metal having a small work function such as aluminum be used to produce the source electrode and the drain electrode.

Furthermore, the present invention provides an electronic apparatus including the organic electronic device. Examples of the electronic apparatus include, but are not limited to, display apparatuses, memory devices, smart cards, sensors, and electronic tags (RFID).

MODE FOR THE INVENTION

Hereinafter, the present invention will be described in detail in light of Examples. The present invention may, however, be embodied in many different forms and should not be construed as being limited to the Examples set forth herein. Rather, these Examples are provided such that this disclosure will be thorough and complete and will fully convey the concept of the present invention to those skilled in the art.

Synthetic Example 1

The compound that was used as the polyheterocyclic compound of the present invention and represented by Formula 1-7 was produced by using the procedure of the following reaction scheme 1.

<reaction scheme 1>

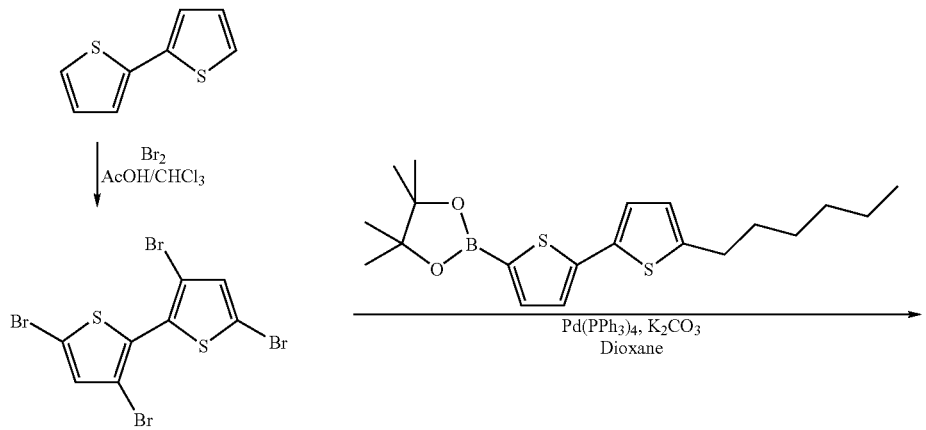

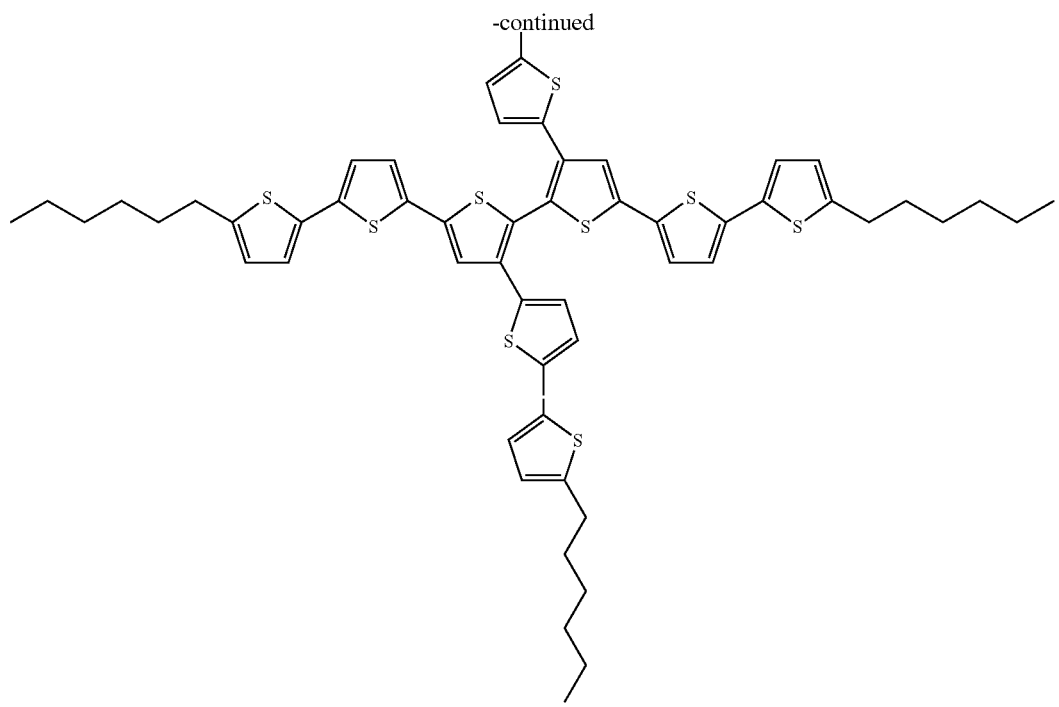

A detailed description of the reaction will be given. 2,2'-bithiophene (30 mmol, 5 g) was dissolved in acetic acid (100 ml) and chloroform (75 ml) and then cooled with an ice. A solution in which bromine (60.5 mmol, 9.65 g) was dissolved in chloroform (50 ml) was added to the former solution mixture for about 40 min in drops, and the same amount of bromine was added at normal temperature for 1 hour in drops. The resulting solution mixture was agitated at normal temperature for 12 hours and then recycled for 24 hours. After the solvent was removed by using distillation at reduced pressure, re-crystallization was performed using ethanol to obtain 15 g of 30 mmol 3,3', 5,5'-tetrabromo-2,2'-bithiophene at a yield of 100%.

GC-MS Calcd. for $C_8H_2Br_4S_2$ [M$^+$]: 482, Found: 482. $^1$H NMR (DMSO-d6): δ 7.5 (s, 2H).

3,3', 5,5'-tetrabromo-2,2'-bithiophene (2.2 mmol, 1.0 g) and 5-hexyl-5'-(4,4,5,5-tetramethyl-1,3,2-dioxaborolan-2-yl)-2,2'-bithiophene (12.5 mmol, 3.6 g) were dissolved in dioxane (50 ml), 2M $K_2CO_3$ aqueous solution (30 mmol, 15 ml) and tetrakis(triphenyl-phosphine)palladium (0) (0.3 mmol, 0.34 g) were added thereto, and reflux was performed in a nitrogen atmosphere for 24 hours. After the reaction was finished, chloroform and distilled water were poured to separate and extract the organic layer. After the separated organic layer was dried with anhydrous $MgSO_4$, the solvent was removed by using distillation at reduced pressure to obtain a product mixture. After the mixture was purified by means of column chromatography using toluene and hexane (1/3, v/v) as a developing solvent, recrystallization was performed with hexane to obtain 2.1 g of 3.1 mmol compound represented by Formula 1-7 at a yield of 63%.

APCI-MS Calcd. for $C_{64}H_{70}S_{10}$ [M+H$^+$]: 1159, Found: 1159. $^1$H NMR (CDCl$_3$): δ 7.3 (s, 2H), 7.2 (s, 2H), 7.1 (d, 2H), 7.0 (t, 4H), 6.9 (d, 2H), 6.8 (m, 4H), 6.7 (d, 2H), 6.6 (d, 2H), 6.6 (d, 2H), 2.8 (t, 2H), 2.7 (t, 2H), 1.6~1.7 (m, 8H), 1.4~1.2 (m, 24H), 0.8 (m, 12H).

Example 1

Production of Organic Thin Film Transistor

The n-doped silicon wafer was used as the substrate and the gate electrode. Silicon dioxide (SiO$_2$) was deposited on the n-doped silicon wafer by heating to form a silicon dioxide (SiO$_2$) insulating layer 12 to a thickness of 300 nm. The source electrode and the drain electrode made of gold (Au) were formed on the silicon dioxide (SiO$_2$) insulating layer 12 by using a shadow mask. The semiconductor layer was formed on the source electrode and the drain electrode on the substrate by using the solution process. In this connection, a channel width (W) and a channel length (L) were set to 1□ and 100□, respectively. The compound that was produced in Synthetic Example 1 was dissolved in chloroform (CHCl$_3$) at a concentration of 3 wt % and spin coating was performed at a speed of 1000 rpm for 20 sec to form the semiconductor layer. Additionally, the contact that coated to the semiconductor layer was dried at 85° C. for 10 min to produce an organic thin film transistor having a bottom-contact structure, shown in FIG. 2, of a bottom-gate.

Comparative Example 1

The device was produced by using the same method as Example 1, except that poly[3-hexylthiophene] (manufactured by Aldrich, Inc., regioregular grade) was used to form the semiconductor layer 14. The spin coating condition was as follows. Poly[3-hexylthiophene] was dissolved in chloroform (CHCl$_3$) at a concentration of 0.5 wt %, spin coating was performed at a speed of 1000 rpm for 20 sec, and drying was performed at 100° C. for 10 min to produce an organic thin film transistor.

Experimental Example

Output characters and transport characters were evaluated in order to obtain electric properties by using the organic thin film transistor that was produced in Example 1 and Comparative Example 1. The gate voltage ($V_G$) was applied to the organic thin film transistors that were produced in Example 1 and Comparative Example 1 while the gate voltage was changed to measure a change in drain-source current ($I_{DS}$) to drain-source voltage ($V_{DS}$), and the results are shown in FIGS. 4 and 5. FIG. 4 shows a saturation state in which $I_{DS}$ according to the gate voltage is maintained at a pre-determined point regardless of $V_{DS}$. However, in FIG. 5, $I_{DS}$ is not saturated but increased in proportion to $V_{DS}$. Accordingly, the performance of the organic thin film transistor of Example 1 is better than that of Comparative Example 1.

As shown in FIG. 6, in respects to the threshold voltage, there is a significant change between before and after $V_G$ becomes 0, and $I_{DS}$ is significantly changed to rapidly change the slope. However, in FIG. 7, in respects to the threshold voltage, there is a change at a point where $V_G$ is 80, but $I_{DS}$ is not apparently changed. Therefore, from the transport characteristic graph of Example 1, it can be seen that the switching performance of the organic thin film transistor of the present invention is excellent.

From the results of the measured electric properties, it can be seen that the measured field-effect mobility ($\mu_{FET}$) of Example 1 was found to be $1.53 \times 10^{-3}$ □/Vs and the measured on/off current ratio was found to be $7.26 \times 10^3$ in the saturation state of drain-source current, and the measured field-effect mobility ($\mu_{FET}$) of Comparative Example 1 was found to be $1.27 \times 10^{-3}$ □/Vs and the measured on/off current ratio was found to be $3.68 \times 10^1$. From the results, it can be seen that the organic thin film transistor where the polyheterocyclic compound of the present invention is used as the organic semiconductor has excellent performance such as the high field-effect mobility and on/off current ratio.

The invention claimed is:

1. A polyheterocyclic compound represented by Formula 1:

[Formula 1]

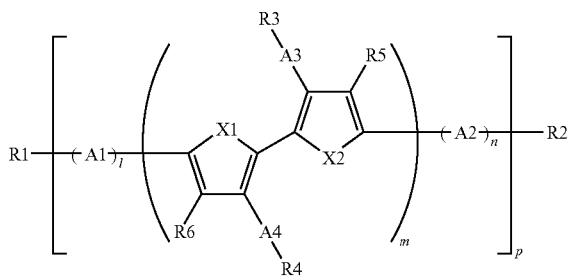

wherein m is an integer in the range of 1 to 5, l and n are each independently an integer in the range of 0 to 5, p is an integer in the range of 1 to 10,000, X1 and X2 are each independently any one selected from the group consisting of S, O, NH, and NR, in which R of NR is any one selected from the group consisting of a substituted or unsubstituted $C_1$-$C_{60}$ alkyl group and a substituted or unsubstituted $C_6$-$C_{20}$ aryl group, A1 and A2 are each independently any one selected from the group consisting of a substituted or unsubstituted alkenyl group, a substituted or unsubstituted alkynyl group, a substituted or unsubstituted arylamine group, a substituted or unsubstituted aromatic or nonaromatic heterocyclic group, and a substituted or unsubstituted $C_6$-$C_{20}$ aryl group, A3 and A4 are each independently any one selected from the group consisting of a substituted or unsubstituted arylamine group, and a substituted or unsubstituted aromatic or nonaromatic heterocyclic group, and R1 to R6 are each independently any one selected from the group consisting of a hydrogen atom, halogen, a substituted or unsubstituted straight- or branch-chained $C_1$-$C_{12}$ alkyl group, a substituted or unsubstituted straight- or branch-chained $C_1$-$C_{12}$ alkoxy group, a substituted or unsubstituted straight- or branch-chained $C_1$-$C_{12}$ thioalkyl group, a substituted or unsubstituted arylamine group, a substituted or unsubstituted aromatic or nonaromatic heterocyclic group, and a substituted or unsubstituted $C_6$-$C_{20}$ aryl group.

2. The polyheterocyclic compound according to claim 1, wherein at least one of X1 and X2 is S in Formula 1.

3. The polyheterocyclic compound according to claim 1, wherein A1 to A4 are each independently a substituted or unsubstituted conjugated group in Formula 1.

4. The polyheterocyclic compound according to claim 1, which is represented by Formula 2 or 3:

[Formula 2]

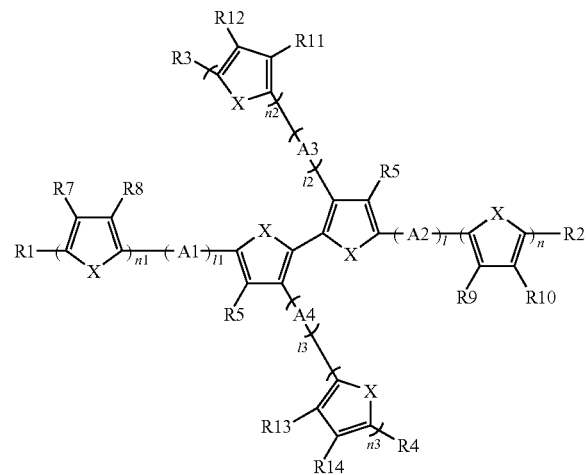

wherein l, l1, l2, l3, n, n1, n2, and n3 are each independently an integer in the range of 0 to 5, X is any one selected from the group consisting of S, O, NH, and NR, a plurality of Xs may be the same as or different from each other, in which R of NR is any one selected from the group consisting of a substituted or unsubstituted $C_1$-$C_{60}$ alkyl group and a substituted or unsubstituted $C_6$-$C_{20}$ aryl group, A1 and A2 are each independently any one selected from the group consisting of a substituted or unsubstituted alkenyl group, a substituted or unsubstituted alkynyl group, a substituted or unsubstituted arylamine group, a substituted or unsubstituted aromatic or nonaromatic heterocyclic group, and a substituted or unsubstituted $C_6$-$C_{20}$ aryl group, A3 and A4 are each independently any one selected from the group consisting of a substituted or unsubstituted arylamine group, and a substituted or unsubstituted aromatic or nonaromatic heterocyclic group, and R1 to R14 are each independently any one selected from the group consisting of a hydrogen atom, halogen, a substituted or unsubstituted straight- or branch-chained $C_1$-$C_{12}$ alkyl group, a substituted or unsubstituted straight- or branch-chained $C_1$-$C_{12}$ alkoxy group, a substituted or unsubstituted straight- or branch-chained $C_1$-$C_{12}$ thioalkyl group, a substituted or unsubstituted arylamine group, a substituted or unsubstituted aromatic or nonaromatic heterocyclic group, and a substituted or unsubstituted $C_6$-$C_{20}$ aryl group,

[Formula 3]

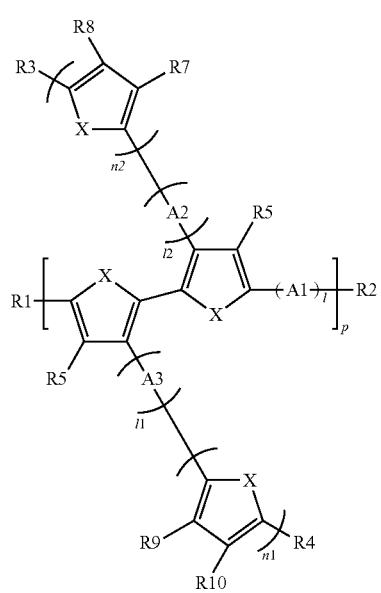

wherein l, l1, l2, n1, and n2 are each independently an integer in the range of 0 to 5 and p is an integer in the range of 1 to 10,000, X is any one selected from the group consisting of S, O, NH, and NR, a plurality of Xs may be the same as or different from each other, in which R of NR is any one selected from the group consisting of a substituted or unsubstituted $C_1$-$C_{60}$ alkyl group and a substituted or unsubstituted $C_6$-$C_{20}$ aryl group, A1 is any one selected from the group consisting of a substituted or unsubstituted alkenyl group, a substituted or unsubstituted alkynyl group, a substituted or unsubstituted arylamine group, a substituted or unsubstituted aromatic or nonaromatic heterocyclic group, and a substituted or unsubstituted $C_6$-$C_{20}$ aryl group, A2 and A3 are each independently any one selected from the group consisting of a substituted or unsubstituted alkenyl group, a substituted or unsubstituted arylamine group, and a substituted or unsubstituted aromatic or nonaromatic heterocyclic group, and R1 to R10 are each independently any one selected from the group consisting of a hydrogen atom, halogen, a substituted or unsubstituted straight- or branch-chained $C_1$-$C_{12}$ alkyl group, a substituted or unsubstituted straight- or branch-chained $C_1$-$C_{12}$ alkoxy group, a substituted or unsubstituted straight- or branch-chained $C_1$-$C_{12}$ thioalkyl group, a substituted or unsubstituted arylamine group, a substituted or unsubstituted aromatic or nonaromatic heterocyclic group, and a substituted or unsubstituted $C_6$-$C_{20}$ aryl group.

5. The polyheterocyclic compound according to claim 1, which is any one of compounds represented by Formulae 1-1 to 1-7, 1-9, and 1-11 to 1-25:

[Formula 1-1]

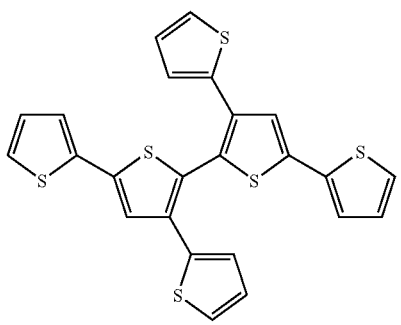

[Formula 1-2]

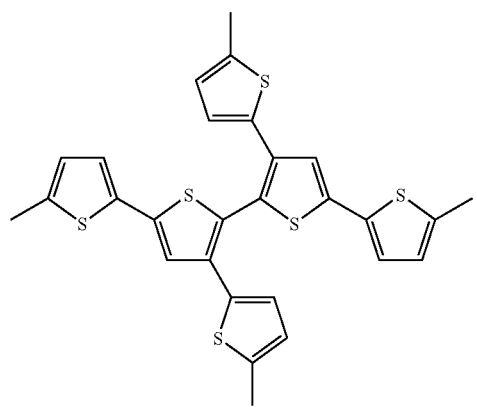

[Formula 1-3]

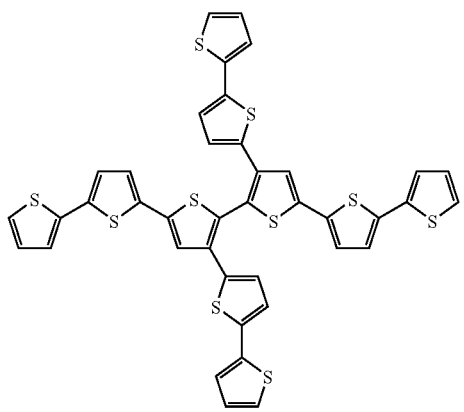

[Formula 1-4]
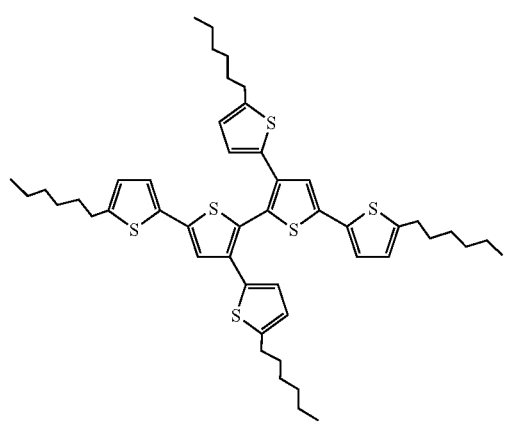
[Formula 1-5]
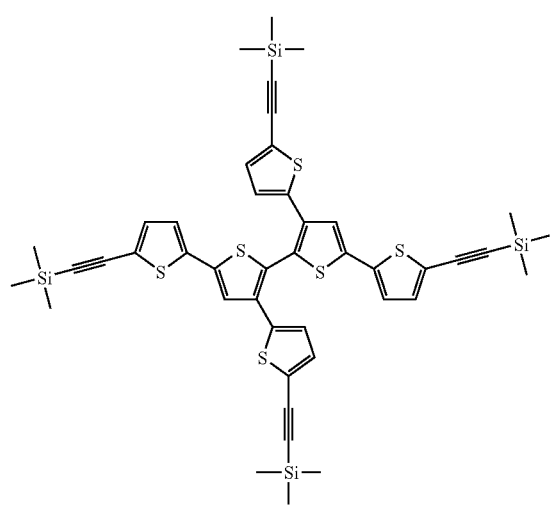
[Formula 1-6]
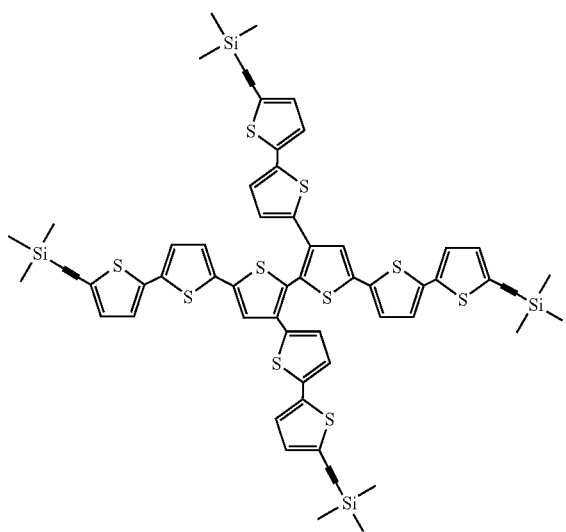
[Formula 1-7]
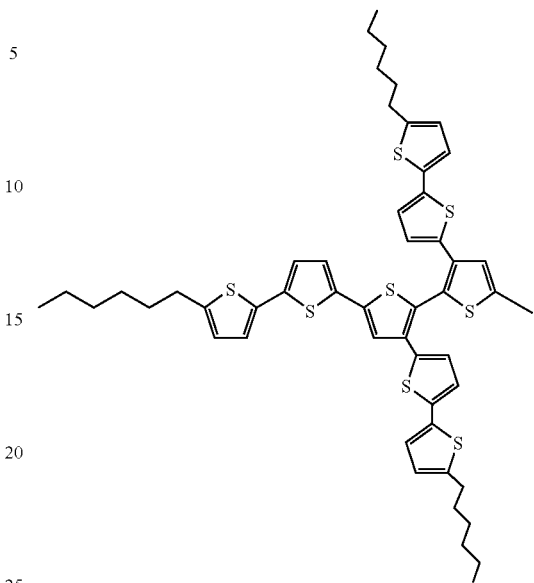
[Formula 1-8]
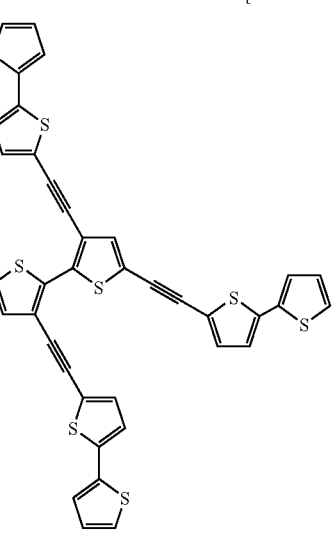

[Formula 1-9]
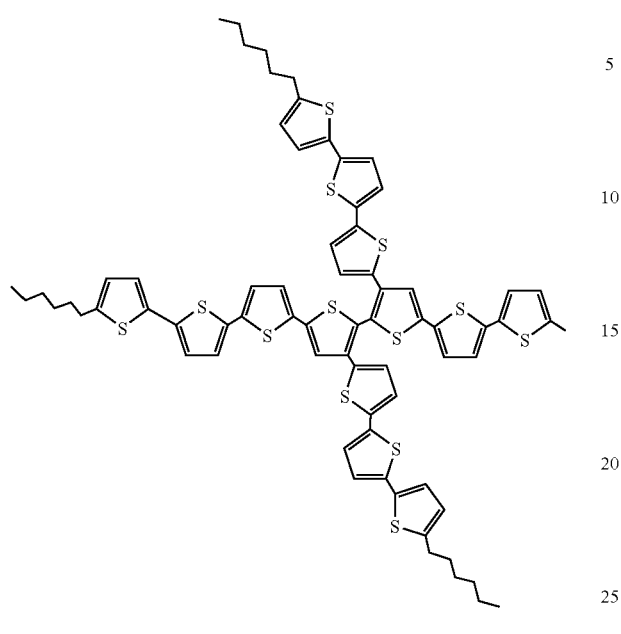
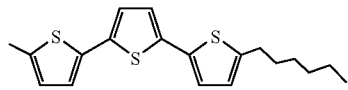
[Formula 1-10]
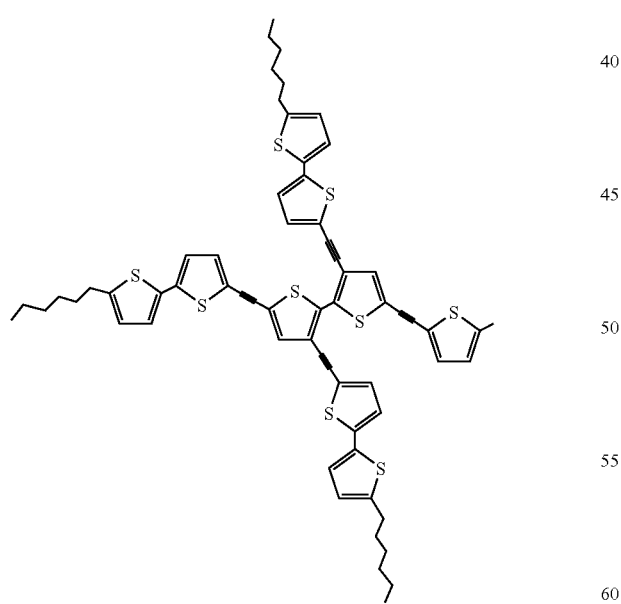
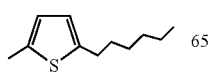
[Formula 1-11]
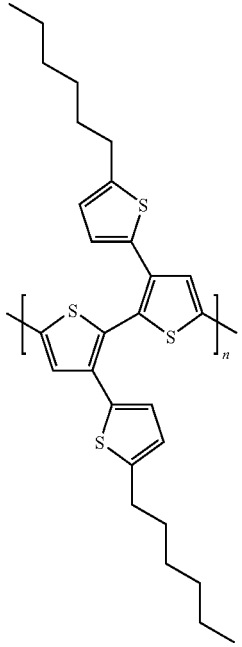
[Formula 1-12]
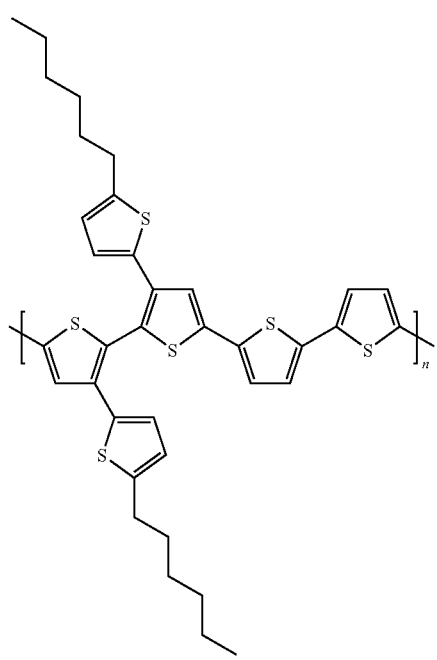

[Formula 1-13]
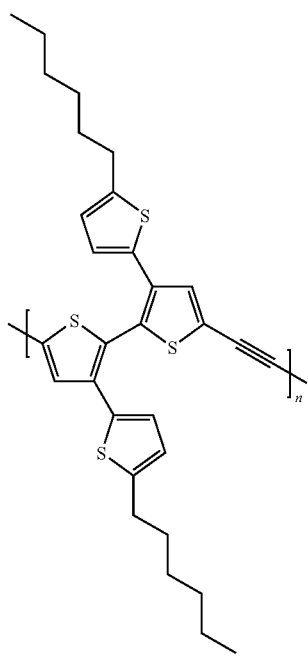
[Formula 1-14]
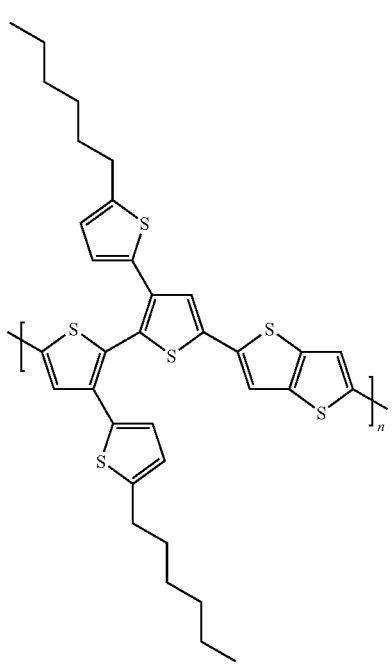
[Formula 1-15]
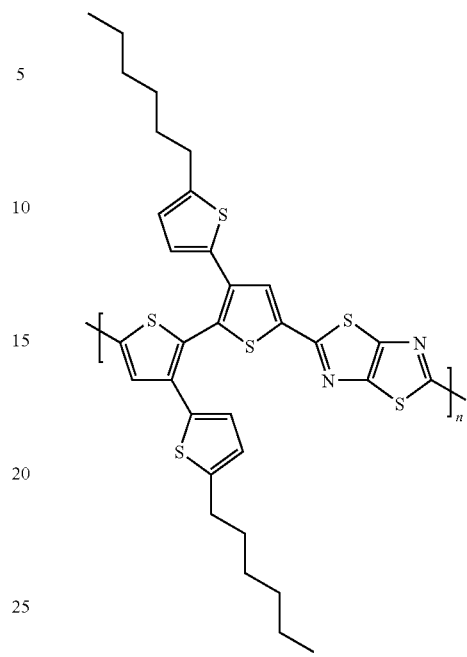
[Formula 1-16]
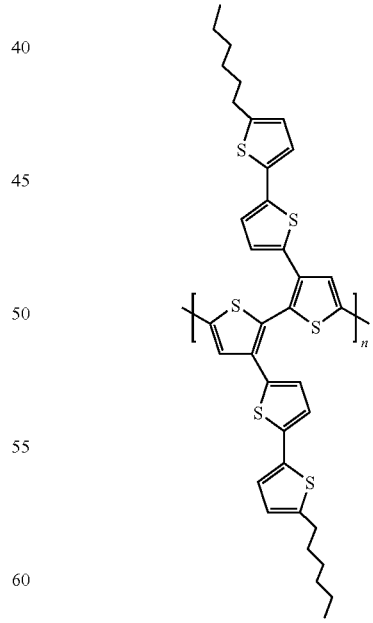

[Formula 1-17]
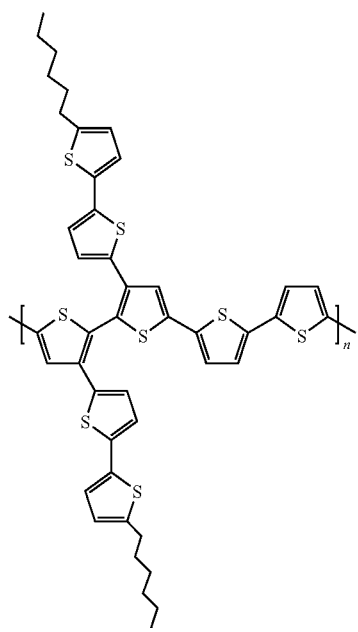
[Formula 1-18]
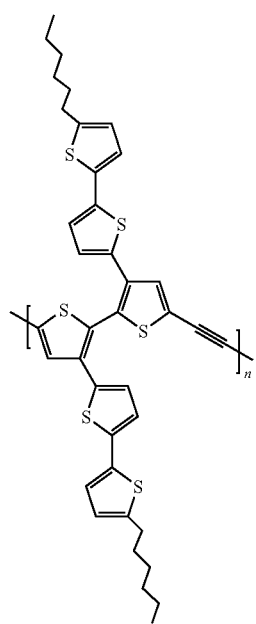
[Formula 1-19]
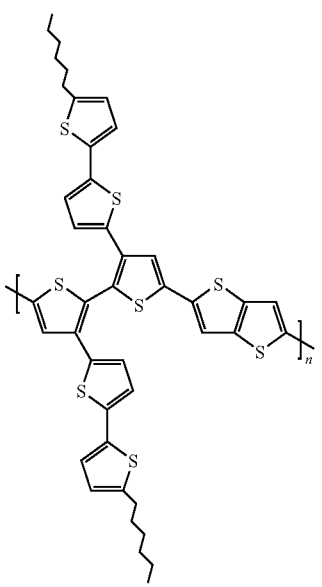
[Formula 1-20]
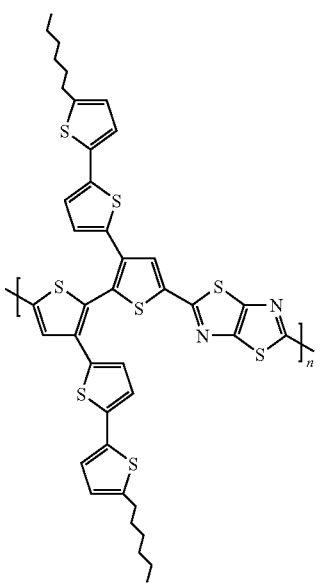

[Formula 1-21]
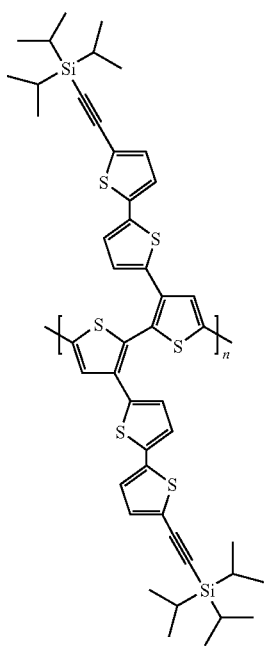
[Formula 1-23]
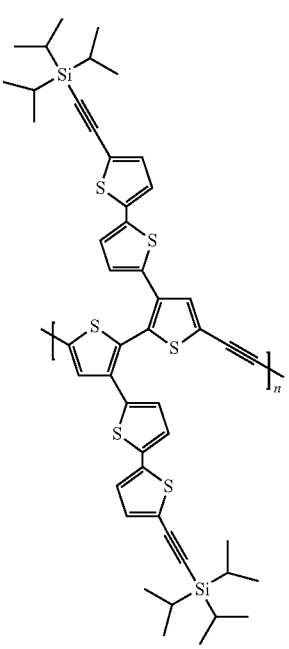
[Formula 1-22]
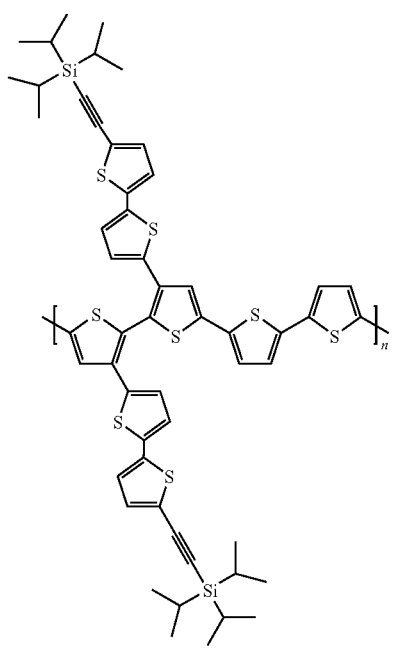
[Formula 1-24]
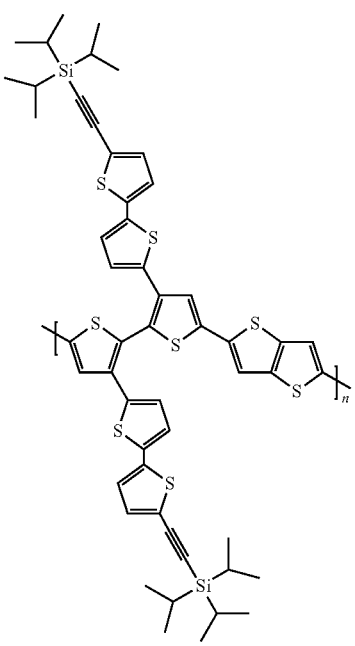

-continued

[Formula 1-25]

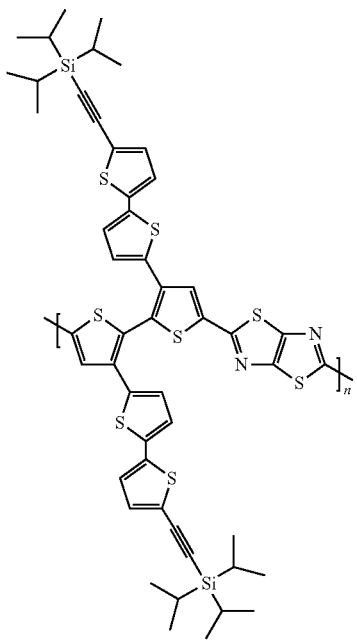

6. An organic electronic device using the polyheterocyclic compound according to claim 1 as an organic semiconductor substance.

7. The organic electronic device according to claim 6, wherein any one solution process selected from the group consisting of screen-printing, ink-jet printing, micro-contact printing, spin coating, dip coating, and SAM (self-assembled monolayer) is performed by using the polyheterocyclic compound to form an organic semiconductor layer.

8. The organic electronic device according to claim 6, which is selected from the group consisting of an organic thin film transistor, an organic light emitting diode, an organic solar cell, an organic laser, an electromagnetic wave blocking film, a capacitor, and a memory device.

9. An electronic apparatus including an organic electronic device using the polyheterocyclic compound according to claim 1 as an organic semiconductor substance.

10. An electronic apparatus including an organic thin film transistor using the polyheterocyclic compound according to claim 1.

11. The electronic apparatus according to claim 9, which is selected from the group consisting of a display apparatus, a memory device, a smart card, a sensor, and an electronic tag (RFID).

* * * * *